United States Patent
Mabondzo et al.

(10) Patent No.: US 12,296,046 B2
(45) Date of Patent: May 13, 2025

(54) MICRO-EMULSION CONTAINING CREATINE FATTY-ESTER, METHOD FOR PREPARING SAID MICRO-EMULSION AND USES THEREOF

(71) Applicant: COMMISSARIAT À L'ÉNERGIE ATOMIQUE ET AUX ÉNERGIES ALTERNATIVES, Paris (FR)

(72) Inventors: Aloïse Mabondzo, Paris (FR); Gabriela Ullio-Gamboa, Gif s/ Yvette (FR); Sophie Dezard, Forges les Bains (FR); Frédéric Taran, Gif s/ Yvette (FR); Anne-Cécile Guyot, Rueil-Mal-Maison (FR); Olivier Loreau, St Michel s/ Orge (FR); Henri Benech, Paris (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 116 days.

(21) Appl. No.: 17/051,215

(22) PCT Filed: May 2, 2019

(86) PCT No.: PCT/EP2019/061293
§ 371 (c)(1),
(2) Date: Oct. 28, 2020

(87) PCT Pub. No.: WO2019/211399
PCT Pub. Date: Nov. 7, 2019

(65) Prior Publication Data
US 2021/0128467 A1    May 6, 2021

(30) Foreign Application Priority Data

May 3, 2018   (EP) .................................. 18305557

(51) Int. Cl.
*A61K 31/202* (2006.01)
*A61K 9/107* (2006.01)
(Continued)

(52) U.S. Cl.
CPC .......... *A61K 9/1075* (2013.01); *A61K 31/202* (2013.01); *A61K 31/221* (2013.01); *A61K 9/0043* (2013.01)

(58) Field of Classification Search
None
See application file for complete search history.

(56) References Cited

U.S. PATENT DOCUMENTS

2002/0049253 A1   4/2002  Kaddurah-Daouk
2003/0212130 A1  11/2003  Miller et al.
(Continued)

FOREIGN PATENT DOCUMENTS

EP   0589843 A1    3/1994
EP   2692719 A1 *  2/2014  ........... A23L 33/175
(Continued)

OTHER PUBLICATIONS

Cordingley et al., Anti-Inflammatory and Anti-Catabolic Effects of Creatine Supplementation: A Brief Review, Nutrients, 14 , 544. (Year: 2022).*

(Continued)

*Primary Examiner* — Alton N Pryor
(74) *Attorney, Agent, or Firm* — Chrisman Gallo Tochtrop LLC

(57) ABSTRACT

A composition in the form of a micro-emulsion composed of an oil phase comprising at least one omega 3 fatty acid or salt thereof and at least one glyceride, an aqueous phase and one or more non ionic surfactant(s), said composition containing at least one creatine fatty ester or salt thereof. Further, a method for preparing such a composition and its (Continued)

Figure 1:
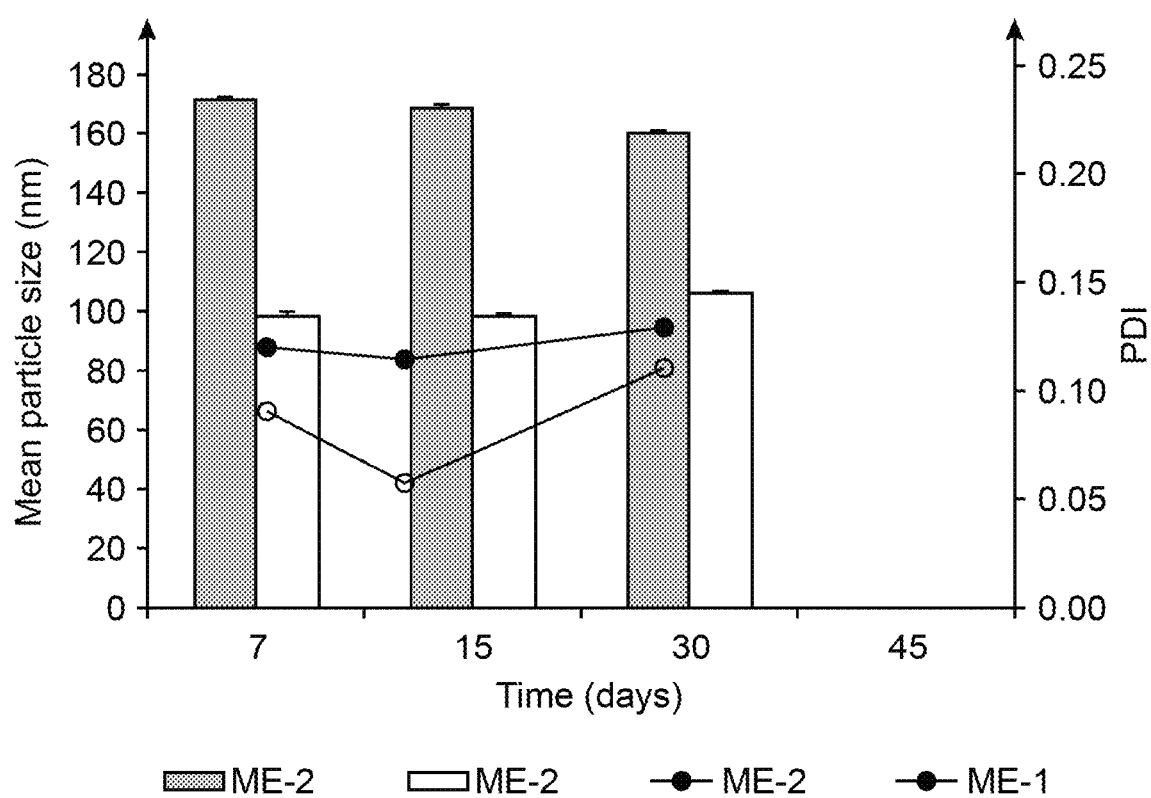
Figure 2A:
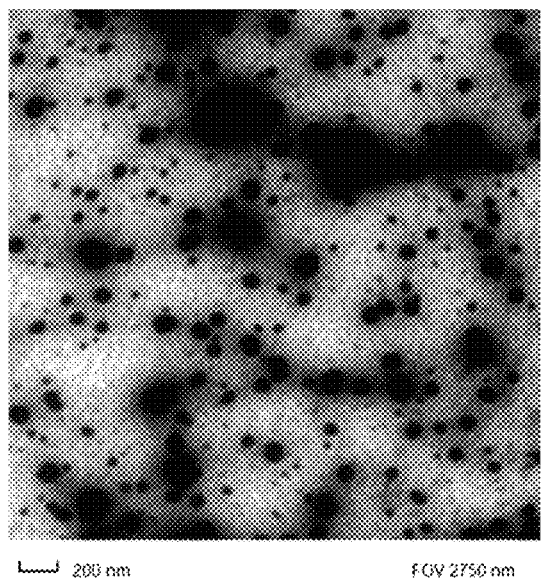
Figure 2B:
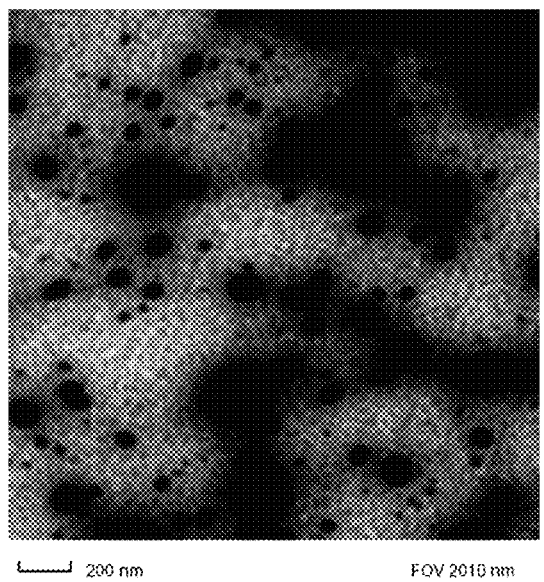
Figure 2C:
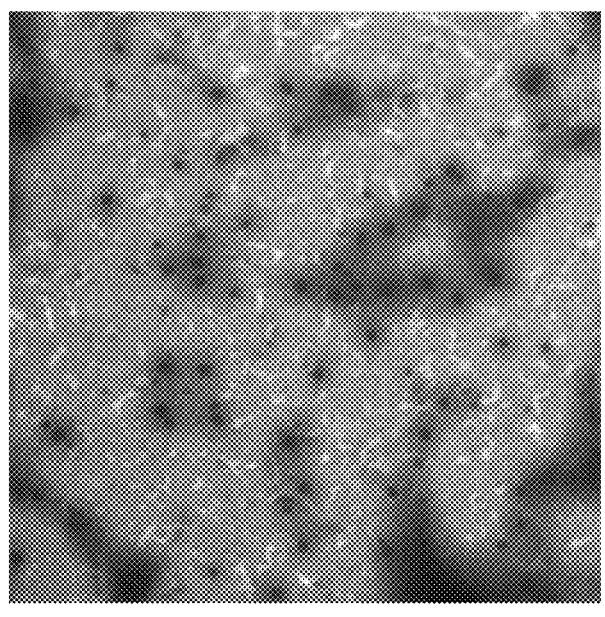
Figure 2D:
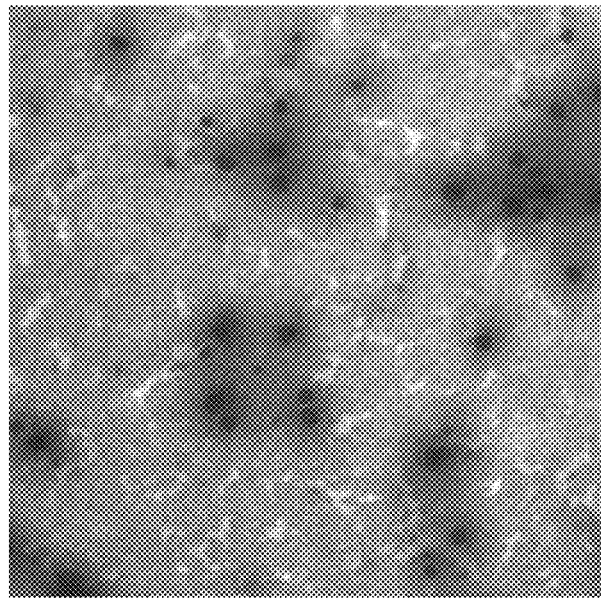

use in medicine in particular for treating the brain creatine transporter deficiency disease.

25 Claims, 3 Drawing Sheets

(51) Int. Cl.
*A61K 31/221* (2006.01)
*A61K 9/00* (2006.01)

(56) References Cited

U.S. PATENT DOCUMENTS

| | | | |
|---|---|---|---|
| 2010/0034880 A1* | 2/2010 | Sintov | A61K 9/0014 |
| | | | 424/484 |
| 2015/0238453 A1 | 8/2015 | Qwoc | |
| 2017/0165264 A1* | 6/2017 | Renshaw | A61K 31/7068 |

FOREIGN PATENT DOCUMENTS

| | | |
|---|---|---|
| JP | 2001525363 A * | 12/2001 |
| WO | 02/22135 A1 | 3/2002 |
| WO | 2015/120299 A1 | 8/2015 |

OTHER PUBLICATIONS

Kley RA, Tarnopolsky MA, Vorgerd M. Creatine for treating muscle disorders. Cochrane Database Syst Rev. Jun. 5, 2013;2013(6) (Year: 2013).*

Balestrino M. Role of Creatine in the Heart: Health and Disease. Nutrients. Apr. 7, 2021;13(4):1215. (Year: 2021).*

Tran NT, Kowalski GM, Muccini AM, Nitsos I, Hale N, Snow RJ, Walker DW, Ellery SJ. Creatine supplementation reduces the cerebral oxidative and metabolic stress responses to acute in utero hypoxia in the late-gestation fetal sheep. J Physiol. Jul. 2022; 600(13):3193-3210. (Year: 2022).*

Physio Matters, Joint Article: creatine in Neuro Rehabilitation, obtained online at: https://www.physio-matters.org/creatine-in-neuro-rehabilitation/#:~:text=Creatine%20in%20stroke&text=This% 20minimises%20any%20secondary%20brain,the%20brain%20tissue% 20%5B9%5D. downloaded on Oct. 15, 2022. (Year: 2022).*

Mayo Clinic, Creatine, obtained online at: https://www.mayoclinic.org/drugs-supplements-creatine/art-20347591?p=1, downloaded on Oct. 15, 2022. (Year: 2022).*

Gattfosse, New Maisine CC, obtained online at: https://www.gattefosse.com/back/files/Gattefosse%20New%20Maisine%20CC% 20a%20unique%20pharmaceutical%20oil%20for%20solubility% 20and%20oral%20bioavailability%20enhancement%20Oct%202016. pdf, downloaded on Oct. 13, 2022. (Year: 2016).*

Stöckler, Sylvia et al, "Cerebral creatine deficiency syndromes. Clinical aspects, treatment and pathophysiology", IN: Subcell. Biochem., 2007, vol. 46, pp. 149-166.

Van De Kamp, Jiddeke et al. "X-linked creatine transporter deficiency: clinical aspects and pathophysiology", In: J Inherit Metab Dis., 2014, vol. 37, pp. 715-733.

Kurosawa, Yuko et al, "Cyclocreatine treatment improves cognition in mice with creatine transporter deficiency", IN: Journal of Clinical Investidation, 2012, vol. 122, No. 8, pp. 2837-2846.

Trotier-Faurion, Alexandra et al., "Synthesis and biological evaluation of new creatine fatty esters revealed dodecyl creatine ester as a promising drug candidates for the treatment of the creatine transporter deficiency", IN: Journal of Medicinal Chemistry., Jun. 2013, vol. 56, No. 12, pp. 5173-5181.

Trotier-Faurion, Alexandra et al, 2015, "Dodecyl creatine ester and lipid nanocapsule: a double strategy for the treatment of creatine transporter deficiency", IN: Nanomedicine, Jan. 1, 2015, vol. 10, No. 2 pp. 185-191.

Trotier-Faurion, Alexandra et al. "Optimisation pharmacologique des dérivés de la créatine pour le traitement du déficit en transporteur de la créatine", Thèse, Sciences Agricoles, Université Paris XI, Mar. 29, 2013, pp1-390.

Roger, Emilie et al., "Development and characterization of a novel lipid nanocapsule formulation of Sn38 for oral administration", IN: European Journal of Pharmaceutics and Biopharmaceutics, Jan. 31, 2011, vol. 79, No. 1, pp. 181-188.

International Search Report for PCT/EP2019/061293 dated Aug. 6, 2019.

Written Opinion of the International Searching Authority for PCT/EP2019/061293 dated Aug. 6, 2019.

European Search Report for EP18305557 dated Oct. 15, 2018.

* cited by examiner

MICRO-EMULSION CONTAINING CREATINE FATTY-ESTER, METHOD FOR PREPARING SAID MICRO-EMULSION AND USES THEREOF

CROSS-REFERENCE TO RELATED APPLICATIONS

This is a National Stage application of PCT international application PCT/EP2019/061293, filed on May 2, 2019, which claims the priority of European Patent Application No. 18305557.3, filed May 3, 2018, both of which are incorporated herein by reference in their entirety.

TECHNICAL FIELD

The present invention concerns the general field of systems for administering active ingredients and more particularly a composition in the form of a micro-emulsion containing creatine derivatives such as creatine fatty esters and salts thereof.

The present invention also concerns said composition in the form of a micro-emulsion for use in medicine and in particular in treating Creatine Transporter Deficiency (CTD) by nasal administration and process for preparation of said composition in the form of a micro-emulsion.

STATE OF THE PRIOR ART

Creatine (Cr) is an endogenous nutrient produced naturally by the liver and kidneys in most vertebrates. Creatine also known as 2-1(methylguanidino) acetic acid is represented by the following formula (I):

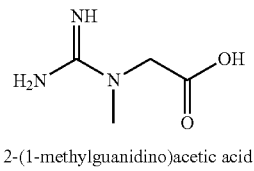

2-(1-methylguanidino)acetic acid

Creatine can also be represented by the following formula (I'):

(NH$_2$)—C(NH)—N(CH$_3$)—CH$_2$—COOH (I')

The uses of creatine are many, including use as supplement to increase muscle mass and enhance muscle performance as well as in emerging applications in the treatment of various disorders such as, without limitation, various neuromuscular disorders, hypoxia and ischemic brain diseases such as stroke, heart disease, various muscular dystrophies [1], various skin disorders [2] and inflammation [3].

In addition the International application WO 2015/120299 proposes a neutraceutical or pharmaceutical composition for treating depression and anxiety-related disorders by acting on the metabolic integrity and capacity of mitochondria [4]. This composition comprises (a) at least one creatine or creatine analog, (b) at least one omega-3 fatty acid such as, for example, docosahexaenoic acid (DHA) and (c) citicoline. Among the creatine analogs, creatine esters, in particular creatine alkyl esters and more particularly creatine ethyl ester are cited. The pharmaceutical compositions disclosed in [4] are suitable for oral, rectal, topical and parenteral administration.

The deficits of the metabolism of creatine, include enzymatic deficits of its biosynthesis (deficits in Arginine:Glycine AmidinoTransferase (AGAT) and GuanidinoAcetate MethylTransferase (GAMT) of recessive autonomic transmission) and of its intra-cerebral transport (gene SLC6A8/CT1, related to X chromosome). Indeed Creatine Transporter Deficiency (CTD) is an inherited neurological disease caused by impairment of a cellular creatine transporter. This disorder drastically affects brain function with intellectual disability being the main phenotypic outcome.

Creatine is essential for proper brain function, having a crucial role in energy storage and transmission, and additional roles as anti-apoptotic, anti-oxidant, neuroprotector and neuromodulator [5]. CTD is a very rare disease, with around 110 cases reported in Europe. In CTD, the defective gene (SLC6A8) encodes for the sodium and chloride dependent Creatine Transporter (CrT) whose function is to transport creatine into and out of cells. Insufficient creatine transportation in neuronal cells leads to impaired energy metabolism and possibly neurotransmission defect. It affects primarily the brain, and is mainly characterized by mental retardation, severe speech delay, autistic like behaviour, and seizures, although other symptoms may also be observed like failure to thrive, muscle hypotonia, neurologic and psychiatric complications, cardiac and intestine manifestations. As SLC6A8 deficiency is an X-linked disorder, mainly males are affected, while according to the X-inactivation pattern heterozygous females may have a variable clinical phenotype, with mild neuropsychologic impairment.

Different therapeutic approaches have been experimented worldwide to address the critical issue of absence of creatine in brain cells of CTD patients. Currently, none of these approaches has led to significant benefit for CTD patients. Indeed, administration of pure creatine does not lead to any improvement as this isolated compound cannot penetrate cerebral cells in CTD patients. Administration of creatine precursors has also failed, showing that this therapeutic approach, though efficient for other creatine deficiency disorders (AGAT and GAMT), is not suitable to treat CTD patients. Experimental creatine derivatives have been assessed as well, but they also failed in improving the CTD condition, mainly because of lack of stability and the toxicity of the tested molecules. There is hence currently no treatment for CTD [6,7].

The patent application US 2015/0238453 proposes creatine derivatives with enhanced solubility in order to improve their bioavailability and their in vivo performance in particular to improve the CTD conditions [8]. Among the creatine derivatives disclosed in this application, there are N-acyl creatines and their aliphatic esters. One particular example thereof is one N-acyl creatine in which the acyl group replacing an active hydrogen in the amino group in creatine is DHA. Clearly, the DHA is covalently linked to the creatine or to the creatine aliphatic ester. In addition, the non-aqueous composition comprising the creatine derivatives as defined in [8] can be administrated orally, topically, transdermally or by intravenous route.

The present inventors previously reported that creatine fatty esters such as, for example, dodecyl creatine ester (DCE) might be a good therapeutic option for patients suffering from CrT deficiency. The proposed treatment has been already screened in vitro for Blood Brain Barrier (BBB) translocation, delivery in endothelial and astroglial cells, and conversion of creatine fatty and, in particular, DCE to Cr [9,10]. Preliminary behavioral analysis in CrT−/y mice revealed that DCE (30 mg/kg) significantly improves the performance of animals in the object recognition task after intracerebroventricular administration. These results thus support the value of the pro-drug strategy for treating CTD, using creatine fatty esters with DCE being the most promising lead among them.

However, creatine fatty esters are degraded by plasma esterases in all biological fluids thus an efficient delivery system to target creatine fatty esters to the brain cells is needed to overcome CrT deficiency.

To solve this technical problem, the present inventors incorporated DCE in lipid nanocapsules (LNC) made of biocompatible material with polyethylene glycol present on their surface [11]. The inventors showed that these LNC loaded with DCE could cross in vitro BBB and entered brain endothelial cells. In human fibroblasts lacking CrT, all or part of the DCE was released from the LNC and biotransformed to creatine. Despite these promising results, the preparation of the LNC incorporating creatine fatty esters using Transcutol® (from Gattefossé), needs three cycles of progressive heating and cooling between 60° C. and 90° C. before adding Transcutol® containing creatine fatty esters. Such a process with several steps at high temperatures attempts to the stability of this compound.

Clearly there is a need for a new pharmaceutical development comprising creatine fatty ester or a salt thereof made from safely excipients and easily to scale up for use in medicine and in particular dedicated to the treatment of CTD patients.

DISCUSSION OF THE INVENTION

The present invention improves the above-listed drawbacks and provides a solution to the aforementioned need. Indeed, the inventors have conceived a nanoengineered delivery system based on the use of creatine fatty ester such as dodecyl creatine ester, a glyceride-based oil and an omega-3 fatty ester such as 3 DocosaHexaenoic Acid (DHA), at least one non ionic surfactant and water to create a micro-emulsion for nasal route in order to improve brain performance in creatine transporter knockout (CrT ko) mice.

This nanoengineered delivery system presents a specific characteristic in terms of solubility, stability and preservation of degradation by esterases. Indeed this nanoengineered delivery system makes possible to deliver creatine fatty ester or salt thereof by nasal administration and thus by-assing the BBB and preventing from a degradation by plasmatic enzymes of the creatine fatty ester or salt thereof. In addition, this nanoengineered delivery system is suitable for an industrial scale production.

This approach shall provide the significant increase in the creatine content in the different brain regions and thus to rescue the cognitive function in CTD patients.

More particularly, the present invention concerns a composition in the form of a micro-emulsion composed of (i) an oil phase comprising at least one omega 3 fatty acid or salt thereof and at least one glyceride, (ii) an aqueous phase and (iii) one or more non ionic surfactant(s), said composition containing at least one creatine fatty ester or salt thereof.

The composition according to the present invention is in the form of a micro-emulsion. A micro-emulsion is meant a limpid suspension, thermodynamically stable, of fine droplets of a first liquid in a second liquid that is non-miscible with the first one. The droplets are typically in a size range of 5 nm to 200 nm, giving rise to a micro-emulsion that is transparent or translucent in appearance. When the micro-emulsion is a «water-in-oil micro-emulsion» also called «reverse micro-emulsion», the first liquid is polar and the second one is non polar. Alternatively, when the micro-emulsion is an «oil-in-water micro-emulsion», the first liquid is non polar and the second one is polar. In the micro-emulsions, the polar liquid forms the aqueous phase while the non polar liquid forms the oily phase. Typically, micro-emulsions are clear, thermodynamically stable, isotropic liquid mixtures of oil, water and surfactants frequently in combination with a co-surfactant.

In the present invention, the expressions «hydrophilic phase», «water phase» and «aqueous phase» are equivalent and can be used interchangeably. Similarly, the expressions «hydrophobic phase», «lipophilic phase», «oily phase» and «oil phase» are equivalent and can be used interchangeably.

Typically, the composition according to the present invention is in the form of an oil-in-water micro-emulsion. In an oil-in-water micro-emulsion, the aqueous phase is a continuous phase while the oily phase is a discontinuous phase in the form of droplets. In the composition according to the present invention, the creatine fatty ester(s) or salt(s) thereof is/are dissolved in the droplets of the oil phase. In an alternative embodiment, in the composition according to the present invention, the creatine fatty ester(s) or salt(s) thereof is/are dissolved in the non-ionic surfactant(s). In another alternative embodiment, in the composition according to the present invention, the creatine fatty ester(s) or salt(s) thereof is/are dissolved not only in the oil phase but also in the non-ionic surfactant(s).

The composition according to the present invention contains at least one creatine fatty ester or salt thereof. Advantageously, a creatine fatty ester is represented by the formula (I):

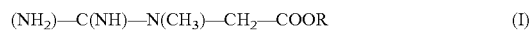

$$(NH_2)-C(NH)-N(CH_3)-CH_2-COOR \quad (I)$$

in which R represents an alkyl radical with 4 to 30 carbon atoms, an alkenyl radical with 4 to 30 carbon atoms, an aryl radical with 6 to 30 carbon atoms or a glucosyl radical optionally substituted.

Regarding R, by «alkyl radical with 4 to 30 carbon atoms» is meant a linear, branched or cyclic (hetero)alkyl group, optionally substituted, with 4 to 30 carbon atoms, notably with 4 to 25 carbon atoms and in particular, with 4 to 20 carbon atoms, the heteroatom(s) of the heteroalkyl group being N, O, P or S.

Regarding R, by «alkenyl radical with 4 to 30 carbon atoms» is meant a linear, branched or cyclic (hetero)alkenyl group, optionally substituted, with 4 to 30 carbon atoms, notably with 4 to 25 carbon atoms and in particular, with 4 to 20 carbon atoms, the heteroatom(s) of the heteroalkenyl group being N, O, P or S.

Regarding R, by «aryl radical with 6 to 30 carbon atoms», is meant a mono- or poly-cyclic (hetero)aromatic group, optionally substituted, having from 6 to 30 carbon atoms, notably from 6 to 25 carbon atoms, in particular, from 6 to 20 carbon atoms, the heteroatom(s) of the heteroaromatic group being N, O, P or S.

Within the scope of the present invention, by «optionally substituted» is meant a radical which can be substituted with one or more groups selected from an alkyl group, an aryl group, an alkoxy group, a halogen, a hydroxy, a cyano, a trifluoromethyl or a nitro. For substitution groups, an «alkyl group» is a linear, branched or cyclic (hetero)alkyl group with 1 to 10 carbon atoms, the heteroatom(s) of the heteroalkyl group being N, O, P or S. For substitution groups, an «aryl group» is a mono- or poly-cyclic (hetero)aromatic group having from 6 to 15 carbon atoms, the heteroatom(s) of the heteroaromatic group being N, O, P or S. For substitution groups, an «alkoxy group» is an oxygen atom substituted by an alkyl group as above defined.

Within the scope of the present invention, by «halogen» is meant a fluorine, chlorine, bromine or iodine.

In what follows, glucose can be represented by the following Fischer formula (II):

$$O=CH-CHOH-CHOH-CHOH-CHOH-CH_2OH \quad (II)$$

Alternatively, glucose can be represented by the formula (III):

(III)

[Structure of glucose pyranose ring with $CH_2OH$ at C6, OH groups at C1, C2, C3, C4, and H atoms]

Regarding R, by «glucosyl radical», is meant a radical of formula $C_6H_{11}O_5$ derived from glucose by elimination of one of the hydroxyl group thereof. The eliminated hydroxyl group can be borne by one of the 5 carbon atoms $C_1$, $C_2$, $C_3$, $C_4$ or $C_6$ (carbon nomenclature refers to formula (III)).

Regarding R, by «substituted glucosyl radical», is meant a glucosyl radical substituted with one or more substitution groups selected from an alkyl group, an aryl group, an alkoxy group, a halogen, a cyano, a trifluoromethyl or a nitro.

In a $1^{st}$ embodiment, the eliminated hydroxyl group is the one of the carbon atom $C_6$ and thus the glucosyl radical can be represented by the following formula (IV):

(IV)

[Structure of glucosyl radical with wavy bond at C6 $CH_2$, OH groups at C1, C3, C4]

In this $1^{st}$ embodiment, a substituted glucosyl radical can be represented by the following formula (V):

(V)

[Structure with $CH_2$ at C6, $OR_1$ at C1, $OR_2$ at C2, $OR_3$ at C3, $R_4O$ at C4]

in which the radicals $R_1$, $R_2$, $R_3$ and $R_4$, identical or different, represent a substitution group as previously defined.

Advantageously, the radicals $R_1$, $R_2$, $R_3$ and $R_4$ are identical groups and notably each represents a benzyl group.

Alternatively, the radicals $R_1$, $R_2$, $R_3$ and $R_4$ represent each a group selected from an alkyl group such as a methyl group or an ethyl group and an aryl group such as a benzyl group. In particular, the radical $R_1$ is a methyl group and the radicals $R_2$, $R_3$ and $R_4$ are benzyl groups.

In a $2^{nd}$ embodiment, the eliminated hydroxyl group is the one of the carbon atom $C_1$ and thus the glucosyl radical can be represented by the following formula (VI):

(VI)

[Structure with $CH_2OH$ at C6, OH groups at C2, C3, C4 and wavy bond at C1]

In this $2^{nd}$ embodiment, a substituted glucosyl radical can be represented by the following formula (VII):

(VII)

[Structure with $CH_2OR_8$ at C6, $OR_5$ at C2, $OR_6$ at C3, $R_7O$ at C4, wavy bond at C1]

in which the radicals $R_5$, $R_6$, $R_7$ and $R_8$, identical or different, represent a substitution group as previously defined.

Advantageously, the radicals $R_5$, $R_6$, $R_7$ and $R_8$ are identical groups and notably each represents a benzyl group.

Alternatively, the radicals $R_5$, $R_6$, $R_7$ and $R_8$ represent each a group selected from an alkyl group such as a methyl group or an ethyl group and an aryl group such as a benzyl group.

In a particular embodiment of the present invention, the radical R present in the creatine fatty ester of formula (I) is represented by the following formula (VIII):

$$-CH_2-R' \quad (VIII)$$

in which R' is chosen in the group consisting of an alkyl radical with 3 to 30 carbon atoms, an alkenyl radical with 3 to 30 carbon atoms and an aryl radical with 6 to 30 carbon atoms.

Regarding R', by «alkyl group with 3 to 30 carbon atoms» is meant a linear, branched or cyclic (hetero)alkyl group, optionally substituted, with 3 to 30 carbon atoms, notably with 3 to 25 carbon atoms and in particular, with 3 to 20 carbon atoms, the heteroatom(s) of the heteroalkyl group being N, O, P or S.

Regarding R', by «alkenyl group with 3 to 30 carbon atoms» is meant a linear, branched or cyclic (hetero)alkenyl group, optionally substituted, with 3 to 30 carbon atoms, notably with 3 to 25 carbon atoms and in particular, with 3 to 20 carbon atoms, the heteroatom(s) of the heteroalkenyl group being N, O, P or S.

In the composition according to the present invention, the creatine fatty ester can be present in the form of a salt of creatine fatty ester.

Within the scope of the present invention, «salt» refers to acid addition salts and base addition salts. Such salts can be formed by conventional means, for example by reaction of a form of free acid or a form of free base of a compound implemented in the invention with one or several equivalents of an appropriate acid or base, optionally in a solvent, or in a medium in which the salt is insoluble, then by extracting said solvent, or said medium, by using conventional techniques (for example in vacuum or by freeze drying). The salts can also be prepared by replacing a counter-ion of a compound implemented in the invention in the form of a salt with another counter-ion, for example by using an appropriate ion-exchange resin.

Especially in the purpose of being administered to a human or animal body, the salts of the compounds implemented in the invention are advantageously pharmaceutically acceptable salts.

In particular, when the compounds implemented in the invention are in the form of a salt, the latter being a salt of an alkali metal, in particular sodium or potassium salt, or salt of alkaline earth metal, in particular magnesium or calcium, or even a salt with an organic amide, more particularly with an amino acid such as arginine or lysine.

When the compounds implemented in the invention which have an amine function are in the form of a salt of this amine, the salt is a salt of inorganic acid such as, for example, hydrochloric acid, sulfuric acid, or hydrobromic acid, or in the form of an organic salt, such as, for example, acetic acid, formic acid, triflic acid, tartaric acid, oxalic acid, citric acid, trifluoroacetic acid or methanesulfonic acid.

Advantageously, the creatine fatty esters and salts thereof implemented in the present invention can present one or more radioisotope(s), in particular chosen from iodine-123, iodine-125, iodine-126, iodine-133, iodine-131, iodine-124, indium-111, indium-113m, bromine-77, bromine-76, gallium-67, gallium-68, ruthenium-95, ruthenium-97, technetium-99m, fluorine-19, fluorine-18, carbon-13, carbon-11, nitrogen-15, nitrogen-13, oxygen-17, oxygen-15, oxygen-14, scandium-47, tellurium-122m, thulium-165, yttrium-199, copper-64, copper-62, gadolidium-68 and rubidium-82.

In the present invention, the composition in the form of a micro-emulsion can contain only one creatine fatty ester or only one salt thereof. Alternatively, the composition can contain at least two different creatine fatty esters, at least two different creatine fatty ester salts or a mixture of at least one creatine fatty ester and at least one creatine fatty ester salt.

As particular examples of creatine fatty esters and salts thereof implemented in the present invention, one can cite DCE or a salt thereof such as, for example, hydrochloride salt of DCE.

In the composition in the form of a micro-emulsion of the invention, the creatine fatty ester(s) and/or salt(s) thereof is/are present in an amount of 0.01% to 6% by weight and in particular of 0.02% to 5.5% by weight based on the total weight of the composition.

The oil phase of the composition according to the present invention comprises a first oily component. This oily component is at least one omega-3 fatty ester or a salt thereof. It should be noted that, in the composition according to the present invention, there is no covalent link between an omega-3 fatty ester or a salt thereof and a creatine fatty ester or a salt thereof.

An omega-3 fatty ester is an unsaturated fatty acid that presents a terminal moiety $CH_3$—$CH_2$—$CH$=$CH$— and that can be represented by the following formula (IX):

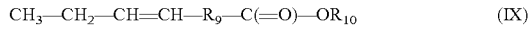

$$CH_3-CH_2-CH=CH-R_9-C(=O)-OR_{10} \quad (IX)$$

in which $R_9$ represents an alkylene chain or an alkenylene chain and in which $R_{10}$ represents H or an alkyl group.

Regarding $R_9$, «alkylene chain» is taken to mean a linear, branched or cyclic alkylene chain, optionally substituted, comprising from 1 to 40 carbon atoms, particularly from 2 to 30 carbon atoms and which can optionally comprise at least one heteroatom. By way of examples of alkylene chains that may be used, methylene, ethylene, n-propylene, isopropylene, butylene, isobutylene, sec-butylene, Cert-butylene, pentylene, isopentylene, hexylene, cyclopentylene, cyclohexylene, —$(CH_2)_n$—O—$(CH_2)_m$—, —$(CH_2)_n$—S—$(CH_2)_m$—, —$(CH_2)_n$—S—S—$(CH_2)_m$—, —$(CH_2)_n$—C(O)O—$(CH_2)_m$— groups may be cited with n and m, identical or different, representing a whole number comprised between 0 and 20. Regarding $R_9$, «alkenylene chain» is taken to mean a linear, branched or cyclic alkenylene chain, optionally substituted, comprising from 3 to 40 carbon atoms and particularly from 4 to 30 carbon atoms and which can optionally comprise at least one heteroatom. By definition, an alkenylene chain comprises at least one carbon carbon double bond. Typically, regarding $R_9$, the alkenylene chain can comprise 1, 2, 3 or 4 carbon carbon double bond(s). As examples of alkenylene chains being able to be used, butenylene, isobutenylene, sec-butenylene, Cert-butenylene, pentenylene, isopentenylene, cyclopentenylene or cyclohexenylene groups may be cited.

Regarding $R_{10}$, «alkyl group» is taken to mean a linear, branched or cyclic alkyl group, optionally substituted, comprising from 1 to 40 carbon atoms, particularly from 2 to 30 carbon atoms and which can optionally comprise at least one heteroatom, the heteroatom(s) of the heteroalkyl group being N, O, P or S.

In the present invention, the composition in the form of a micro-emulsion can contain only one omega-3 fatty ester or only one salt thereof. Alternatively, the composition can contain at least two different omega-3 fatty esters, at least two different omega-3 fatty ester salts or a mixture of at least one omega-3 fatty ester and at least one omega-3 fatty ester salt.

As particular examples of omega-3 fatty esters or salts thereof implemented in the present invention, one can cite linoleic acid, octadecatetraenoic acid, eicosapentaenoic acid, docosahexaenoic acid, docosapentaenoic acid and salt thereof. More particularly, in the composition in the form of a micro-emulsion of the invention, the omega-3 fatty ester implemented is docosahexaenoic acid (DHA) or a salt thereof.

What has been previously explained for a salt of creatine fatty ester also applies to a salt of an omega-3 fatty ester mutatis mutandis. Additional information on salt of an omega-3 fatty ester can also be found in paragraph [0086] of [4].

In the composition in the form of a micro-emulsion of the invention, the first oily component, i.e. omega-3 fatty ester(s) and/or salt(s) thereof, is present in an amount of 4% to 13% by weight and in particular from 5% to 12% by weight based on the total weight of the composition.

The oil phase of the composition according to the present invention also comprises a second oily component. This second oily component is at least one glyceride.

The term «glyceride» refers to an ester of glycerol (1,2, 3-propanetriol) with acyl radicals of fatty acids. Within the present invention, the terms and expression «glyceride», «acylglycerol», «glyceride fatty ester» and «glycerolipid» are equivalent and can be used interchangeably.

In a glyceride, if only one position of the glycerol molecule is esterified with a fatty acid, a «monoglyceride» is produced; if two positions are esterified, a «diglyceride» is produced; and if all three positions of the glycerol are esterified with fatty acids, a «triglyceride» is produced. A glyceride is «simple» if all esterified positions contain the same fatty acid; whereas a glyceride is «mixed» if the esterified positions are substituted with different fatty acids. A glyceride is «complex» if it contains a combination of simple and mixed glycerides.

In the composition according to the present invention, the second oily component is a single glyceride such as a single monoglyceride, a single diglyceride or a single triglyceride. Alternatively, the second oily component is a mixture containing at least two different glycerides such as a mixture containing at least two different monoglycerides, a mixture containing at least two different diglycerides, a mixture containing at least two different triglycerides, a mixture containing at least one monoglyceride and at least one diglyceride, a mixture containing at least one monoglyceride and at least one triglyceride and a mixture containing at least one diglyceride and at least one triglyceride. In a particular embodiment, the second oily component is a mixture containing at least one monoglyceride, at least one diglyceride and at least one triglyceride.

In the glyceride(s) implemented in the composition according to the present invention, the acyl radical(s) comprise(s) from 4 to 36 carbon atoms, advantageously from 5 to 30 carbon atoms and, in particular, from 6 to 24 carbon atoms. This/these acyl radical(s) can be saturated or unsaturated. In the latter case, the acyl radical presents at least one carbon carbon double bond and advantageously 1, 2, 3 or 4 carbon carbon double bonds.

As examples of acyl radicals which can be present in the glyceride(s) of the composition according to the invention, one can cite the acyl groups of the following fatty acids: caproic acid, caprylic acid, capric acid, undecylic acid, lauric acid, myristic acid, tridecylic acid, palmitic acid, margaric acid, stearic acid, nonadecylic acid, arachidic acid, heneicosylic acid, behenic acid, lignoceric acid, cerotic acid, palmitoleic acid, myristoleic acid, linoleic acid, sapienic acid, oleic acid, gadoleic acid, elaidic acid, vaccenic acid, linoelaidic acid, a-linolenic acid, arachidonic acid, eicosapentaenoic acid, erucic acid and docosahexaenoic acid.

The glyceride(s) implemented in the composition according to the present invention can be natural or synthetic. In particular, this/these glyceride(s) are present in vegetable and animal fats and oils and, if necessary, can be extracted therefrom by conventional methods. When the second oily component is a mixture of different glycerides, the latter can be prepared by admixing the different glycerides in appropriate relative proportion. Alternatively this mixture can comprise transesterification products of vegetable oils with glycerol. The one skilled in the art knows methods to perform this transesterification. Additional information on these methods can be found in the patent application EP 0 589 843 [12].

As examples of particular vegetable oils usable as source of glyceride(s) and/or for transesterification, one can cite argan oil, almond oil, avocado oil, beech oil, cashew oil, castor oil, coconut oil, colza oil, corn oil, cottonseed oil, grapefruit seed oil, grape seed oil, hazelnut oil, hemp oil, lemon oil, macadamia oil, mustard oil, olive oil, orange oil, palm oil, peanut oil, pecan oil, pine nut oil, pistachio oil, poppyseed oil, rapeseed oil, rice bran oil, safflower oil, sesame oil, soybean oil, sunflower oil, walnut oil and wheat germ oil.

As particular examples of glyceride or mixture of glycerides which can be used in the composition according to the present invention, one can cite a triglyceride obtained by esterification of caprylic (octanoic) acid and glycerol, such a triglyceride is sold by Abitec Corporation under the trademark CAPTEX 8000;

a mixture of triglycerides, obtained by esterification of glycerol with caprylic (octanoic) and capric (decanoic) acids, such a mixture is sold by Cremer under the trademarks Mygliol 810 and Mygliol 812; it is also sold by Gattefossé under the trademark Labrafac WL1349;

a mixture of monoglycerides, obtained by esterification of glycerol with caprylic (octanoic) and capric (decanoic) acids, such a mixture is sold by Abitec Corporation under the trademark CAPMUL MCM EP;

a mixture of mono-, di- and triglycerides of linoleic ($C_{18:2}$) and oleic ($C_{18:1}$) acids, the diester fraction being preferably predominant, such a mixture is sold by Gattefossé under the trademark MAISINE CC; and a mixture of mono-, di- and triglycerides of oleic ($C_{18:1}$) acid, the monoester fraction being preferably predominant, such a mixture is sold by Gattefossé under the trademark Peceol.

In a particular embodiment, the second oily component is a mixture of mono-, di- and triglycerides of linoleic ($C_{18:2}$) and oleic ($C_{18:1}$) acids, the diester fraction being preferably predominant, such a mixture is sold by Gattefossé under the trademark MAISINE CC.

In the composition in the form of a micro-emulsion of the invention, the second oily component, i.e. the glyceride(s), is present in an amount of 4% to 13% by weight and in particular of 5% to 12% by weight based on the total weight of the composition.

Advantageously, in the composition in the form of a micro-emulsion of the invention, the oil phase is present in an amount of 10% to 20% by weight and in particular of 15% to 18% by weight based on the total weight of the composition.

The composition in the form of a micro-emulsion according to the invention comprises at least one non-ionic surfactant.

Regarding this, non-ionic (or neutral) surfactants are compounds wherein the surfactant properties, particularly the hydrophilic properties, are provided by non-charged functional groups such as an alcohol, an ether, an ester or an amide, and may contain heteroatoms such as nitrogen or oxygen. Due to the low hydrophilic contribution of these functions, the non-ionic surfactants are generally polyfunctional.

The non-ionic surfactant(s) usable in the composition according to the invention can be non-ionic hydrophilic surfactant(s), non-ionic lipophilic surfactant(s) or mixtures thereof.

Within the scope of the present invention, the non-ionic surfactants are particularly selected from the group consisting of alkyl alkoxylates; fatty alcohol alkoxylates; fatty amine alkoxylates; fatty acid alkoxylates; oxo alcohol alkoxylates; alkylphenol alkoxylates; alkyl ethoxylates; fatty acid ethoxylates; fatty amine ethoxylates; fatty acid ethoxylates; oxo alcohol ethoxylates; alkylphenol ethoxylates such as, for example, octylphenol and nonylphenol ethoxylates; alcohols, α-diols, polyethoxylated and polypropoxylated alkylphenols having a fatty chain including, for example, 8 to 18 carbon atoms, the number of ethylene oxide or propylene oxide groups optionally being particularly from 2 to 50; polyoxylglycerides; polyethylene oxides; polypropylene oxides; polyethylene and polypropylene oxide complex polymers; ethylene and propylene oxide copolymers; polyethylene and polypropylene oxide block copolymers such as, for example, POE-POP-POE triblock copolymers; ethylene and propylene oxide condensates on fatty alcohols; polyethoxylated oils; polyethoxylated alcohols; polyethoxylated fatty amides having, preferably, 2 to 30 moles of ethylene oxide; polyethoxylated ethers having, preferably, 2 to 30 moles of ethylene oxide; monoesters (monolaurate, monomyristate, monostearate, monopalmitate, monooleate, etc.) and polyesters of fatty acids and glycerol; polyglycerolated fatty amides comprising on average from 1 to 5 and, more especially, from 1.5 to 4 glycerol groups; oxyethylenated sorbitan fatty acid esters including 2 to 30 moles of ethylene oxide; monoesters (monolaurate, monomyristate, monostearate, monopalmitate, monooleate, etc.) and polyesters of fatty acids and sorbitan, polyoxyethylene sorbitan monoesters; sucrose esters of fatty acids; propylene glycol esters of fatty acids; polyethylene glycol esters of fatty acids; alkyl polyglucosides; N-alkyl glucamine derivatives and amine oxides such as alkyl($C_{10}$-$C_{14}$) amine oxides or N-acylaminopropylmorpholine oxides; polyols (surfactants derived from sugars) in particular glucose alkylates such as for example glucose hexanate; surfactants derived from glucoside (sorbitol laurate) or polyols such as glycerolated alcohol ethers; alkanolamides and mixtures thereof.

Within the scope of the present invention, the non-ionic surfactants are more particularly selected from the group consisting of polyoxyethylene sorbitan monoesters such as, for example, polyoxyethylene (20) sorbitan monooleate (also known as Polysorbate 80 or Tween 80); polyethoxylated oils such as, for example, the polyethoxylated castor oil (sold by BASF under the trademark Kolliphor EL, formerly known as Cremophor EL); polyethylene oxides such as, for example, PEG 400; propylene glycol esters of fatty acids such as, for example, propylene glycol monocaprylate (sold by Gattefossé under the trademark Capryol 90), propylene glycol dicaprylate/caprate (sold by Cremer under the trademark Miglyol 840 or sold by Abitec Corporation under the trademark Captex 200) and propylene glycol monolaurate (sold by Gattefossé under the trademark Lauroglycol FCC); polyoxylglycerides such as, for example, caprylocaproyl polyoxy-8 glycerides (sold by Gattefossé under the trademark Labrasol ALF) or oleoyl polyoxyl-6 glyceride (sold by Gattefossé under the trademark Labrafil M 1944) and polyethoxylated alcohols such as, example, 2(2-ethoxyethoxy)ethanol also known as diethylene-glycol-monoethyl ether (sold by Gattefossé under the trademark Transcutol HP).

The composition in the form of a micro-emulsion according to the invention comprises either a single non-ionic surfactant, or a mixture of non-ionic surfactants i.e. comprising a first non-ionic surfactant and one or more non-ionic co-surfactants. Within the present invention, surfactant and co-surfactant combination may be selected from any non-ionic surfactant types above-listed. As particular example of a mixture of non-ionic surfactants usable in the composition according to the invention, one can cite a mixture of one polyoxylglyceride and one polyethoxylated alcohol such as previously defined. As more particular example of a mixture of non-ionic surfactants usable in the composition according to the invention, one can cite a mixture of oleoyl polyoxyl-6 glyceride (sold by Gattefossé under the trademark Labrafil M 1944) and of 2(2-ethoxyethoxy) ethanol (sold by Gattefossé under the trademark Transcutol HP).

In the composition in the form of a micro-emulsion of the invention, the non-ionic surfactant(s) is/are present in an amount of 50% to 68% and in particular of 58% to 65% by weight based on the total weight of the composition.

The aqueous phase of the composition in the form of a micro-emulsion of the present invention mainly comprises water. In other words, the water generally accounts for at least 70% by weight, at least 80% by weight, at least 90% by weight, at least 95% by weight and at least 80% by weight based on the total weight of the aqueous phase.

In a particular embodiment, the aqueous phase consists of water.

Alternatively, the aqueous phase can comprise at least one additional element. When present, the amount of this/these additional element(s) is typically less than 30% by weight based on the total weight of the aqueous phase. As examples of this/these additional element(s), one can cite an alcohol substance of low molecular weight such as ethanol, glycerol, propanediol or 1,3-butanediol or a thickener.

In the composition in the form of a micro-emulsion of the invention, the aqueous phase is present in an amount of 15% to 30% by weight and in particular of 18% to 27% by weight based on the total weight of the composition.

The present invention also concerns a method for preparing the composition in the form of a micro-emulsion according to the present invention. Any method for preparing such a micro-emulsion can be used in the present invention.

More particularly, the method of the invention comprises the following steps:
a) preparing an oil phase by mixing at least one omega 3 fatty acid or salt thereof as previously defined and at least one glyceride as previously defined,
b) adding, to the oil phase prepared at step (a), at least one creatine fatty ester or salt thereof as previously defined and mixing in order to obtain an oil phase in which at least one creatine fatty ester or salt thereof is dissolved,
c) adding, to the oil phase prepared at step (b), at least one non-ionic surfactant as previously defined and mixing,
d) adding, to the mixture prepared at step (c), an aqueous phase as previously defined and mixing, whereby the composition in the form of a micro-emulsion according to the present invention is obtained.

Alternatively, the method of the invention comprises the following steps:
a') mixing at least one creatine fatty ester or salt thereof as previously defined and at least one glyceride as previously defined,
b') adding, to the mixture prepared at step (a'), at least one omega 3 fatty acid or salt thereof as previously defined and mixing in order to obtain an oil phase in which at least one creatine fatty ester or salt thereof is dissolved,
c') adding, to the oil phase prepared at step (b'), at least one non-ionic surfactant as previously defined and mixing,
d') adding, to the mixture prepared at step (c'), an aqueous phase as previously defined and mixing, whereby the composition in the form of a micro-emulsion according to the present invention is obtained.

Step (a) of the method of the invention is a simple step consisting in preparing an oil phase comprising at least one omega 3 fatty acid or salt thereof as previously defined and at least one glyceride as previously defined. Any technique allowing the preparation of such a phase can be used in the present invention.

Before step (b) or before step (a'), the method may comprise an additional step consisting in preparing the creatine fatty ester(s) and/or salt(s) thereof. The one skilled in the art knows different methods for preparing a creatine fatty ester or a salt thereof.

Some methods involve Brönsted acids-catalyzed reaction of creatine with alcohols. These methods are well adapted to alcohols of low molecular weight such as EtOH, nPrOH, and nBuOH but yield are dramatically reduced in case of fatty, long chain alcohols. Then the method disclosed in [9] and implemented in [10,11] can also be used to prepare creatine fatty esters.

Step (b) of the method of the invention consists in preparing an oil phase comprising at least one omega 3 fatty acid or salt thereof as previously defined, at least one glyceride as previously defined and at least one creatine fatty ester or salt thereof as previously defined.

When the composition according to the invention comprises several creatine fatty esters or salts thereof, these compounds can be added, to the oil phase prepared at step (a) or to the glyceride(s) during step (a'), at a single time or added one after the other or in groups. In the latter case, a mixture of these compounds is advantageously added to the oil phase prepared at step (a) or to the glyceride(s) during step (a').

Mixing during step (b) or during step (a') is conducted under agitation by simple mechanical means using a magnetic bar, a magnetic stirrer such as the magnetic stirrer, Stuart CB162, Bibbly Scientific (Nemours, France), an ultrasound bath, a vortex, a thermomixer such as the thermomixer C, Eppendorf (Montesson, France) or homogenizer. In a particular embodiment, the mixing during step (b) consists in a vortexing step followed by a shaking step performed in a thermomixer. The vortexing step may be carried out at a temperature of between 10° C. and 40° C., advantageously between 15° C. and 30° C. and more particularly at ambient temperature (i.e. 23° C.±5° C.) for a time of between 1 min and 15 min, in particular between 2 min and 10 min, more particularly for about 5 min (i.e. 5 min±1 min). The shaking step may be carried out at a speed of between 500 and 2000 rpm and advantageously at a speed of about 1000 rpm (i.e. 1000 rpm±200 rpm), at a temperature of between 20° C. and 50° C., advantageously between 30° C. and 40° C. and more particularly at a temperature of about 37° C. (i.e. 37° C.±2° C.) for a time of between 12 h and 4 d, in particular between 24 h and 3 d, more particularly for about 48 h (i.e. 48 h±4 h).

Before step (c), before step (b') or before step (c'), the method according to the invention may comprise an additional step consisting in eliminating any undissolved creatine fatty ester or salt thereof from the oil phase obtained after step (b), from the mixture obtained after step (a') or from the oil phase obtained after step (b'). Advantageously, this additional step can comprise a centrifugation step followed by a filtration step. The centrifugation step may be carried out at a speed of between 10 000 g and 30 000 g and advantageously at a speed of about 20 000 g (i.e. 20 000 g±5 000 g), at a temperature of between 4° C. and 40° C., advantageously between 10° C. and 30° C. and more particularly at a temperature of about 20° C. (i.e. 20° C.±2° C.) for a time of between 5 min and 30 min and, in particular for about 15 min (i.e. 15 min±5 min). The supernatant obtained after said centrifugation step is filtered during said filtration step that may be carried out through a 0.22 μm filter. When the method according to the invention comprises a centrifugation step followed by a filtration step, the oil phase implemented at step (c) or at step (b') is the filtrate obtained after the filtration step. Alternatively, the filtrate obtained after filtration can be the mixture implemented at step (b').

Step (b') of the method of the invention is a simple step consisting in adding at least one omega 3 fatty acid or salt thereof as previously defined to the mixture prepared at step (a'). Any technique allowing the preparation of such a phase can be used in the present invention. Mixing during step (b') is conducted under agitation by simple mechanical means using a magnetic bar, a magnetic stirrer such as the magnetic stirrer, Stuart CB162, Bibbly Scientific (Nemours, France), an ultrasound bath, a vortex, a thermomixer such as the thermomixer C, Eppendorf (Montesson, France) or homogenizer. In a particular embodiment, the mixing during step (b') consists in a vortexing step. The vortexing step may be carried out at a temperature of between 10° C. and 40° C., advantageously between 15° C. and 30° C. and more particularly at ambient temperature (i.e. 23° C.±5° C.) for a time of between 15 s and 6 min, in particular between 30 s and 4 min, more particularly for about 1 min (i.e. 1 min±30 s).

Step (c) or step (c') of the method of the invention consists in preparing a mixture of an oil phase comprising at least one omega 3 fatty acid or salt thereof as previously defined, at least one glyceride as previously defined, at least one creatine fatty ester or salt thereof as previously defined and of at least one non-ionic surfactant as previously defined.

When the composition according to the invention comprises several non-ionic surfactants, these compounds can be added, to the oil phase prepared at step (b) or at step (b'), at a single time or added one after the other or in groups. In the latter case, a mixture of these non-ionic surfactants is advantageously added to the oil phase prepared at step (b) or at step (b').

Mixing during step (c) or step (c') is conducted under agitation by simple mechanical means using a magnetic bar, a magnetic stirrer such as the magnetic stirrer, Stuart CB162, Bibbly Scientific (Nemours, France), an ultrasound bath, a vortex, a thermomixer such as the thermomixer C, Eppendorf (Montesson, France) or homogenizer. In a particular embodiment, the mixing during step (c) is carried out thanks to a magnetic stirrer, at a speed of between 100 and 2000 rpm and advantageously at a speed of about 1000 rpm, at a temperature of between 10° C. and 40° C., advantageously between 15° C. and 30° C. and more particularly at ambient temperature (i.e. 23° C.±5° C.) for a time of between 1 min and 20 min, in particular between 2 min and 10 min, more particularly for about 5 min (i.e. 5 min±1 min).

Step (d) or step (d') of the method of the invention consists in adding the aqueous phase as previously defined to the mixture of an oil phase comprising at least one omega 3 fatty acid or salt thereof as previously defined, at least one glyceride as previously defined, at least one creatine fatty ester or salt thereof as previously defined and of at least one non-ionic surfactant as previously defined.

When the aqueous phase of composition according to the invention contains water and at least one additional element as previously defined, the aqueous phase is firstly prepared by mixing the water and at least one additional element before being added to the mixture prepared at step (c) or step (c'). Particularly, the water phase is added dropwise to the mixture prepared at step (c) or step (c').

Mixing during step (d) or step (d') is conducted under agitation by simple mechanical means using a magnetic bar, a magnetic stirrer such as the magnetic stirrer, Stuart CB162, Bibbly Scientific (Nemours, France), an ultrasound bath, a vortex, a thermomixer such as the thermomixer C, Eppendorf (Montesson, France) or homogenizer. In a particular embodiment, the mixing during step (d) is carried out thanks to a magnetic stirrer at a speed of between 100 and 2000 rpm and advantageously at a speed of about 1000 rpm, at a temperature of between 10° C. and 40° C., advantageously between 15° C. and 30° C. and more particularly at ambient temperature (i.e. 23° C.±5° C.) for a time of between 1 min and 20 min, in particular between 2 min and 10 min, more particularly for about 5 min (i.e. 5 min±1 min). Typically, the mixing of step (d) or of step (d') can be stopped as soon as a transparent and homogeneous mixture is obtained.

In another alternative embodiment, the method of the invention comprises the following steps:
- a") mixing at least one creatine fatty ester or salt thereof as previously defined and at least one non-ionic surfactant as previously defined,
- b") adding, to the mixture prepared at step (a"), at least one omega 3 fatty acid or salt thereof as previously defined and at least one glyceride as previously defined and mixing,
- c") adding, to the mixture prepared at step (b"), an aqueous phase as previously defined and mixing, whereby the composition in the form of a micro-emulsion according to the present invention is obtained.

Before step (a"), the method may comprise an additional step consisting in preparing the creatine fatty ester(s) and/or salt(s) thereof. This additional step is as defined for the other alternatives of the method of the invention.

When the composition according to the invention comprises several non-ionic surfactants as previously defined, a mixture of these non-ionic surfactants is advantageously mixed to the creatine fatty ester(s) and/or salt(s) thereof during step (a").

Mixing during step (a") is performed similarly as during step (b) or (a').

At step (b"), the at least one omega 3 fatty acid or salt thereof and the at least one glyceride can be added at a single time or added one after the other or in groups to the mixture prepared at step (a"). In the latter case, a mixture of these compounds is advantageously added to the mixture prepared at step (a").

Mixing during step (b") is conducted under agitation by simple mechanical means using a magnetic bar, a magnetic stirrer such as the magnetic stirrer, Stuart CB162, Bibbly Scientific (Nemours, France), an ultrasound bath, a vortex, a thermomixer such as the thermomixer C, Eppendorf (Montesson, France) or homogenizer. In a particular embodiment, the mixing during step (c) is carried out thanks to a magnetic stirrer, at a speed of between 100 and 2000 rpm and advantageously at a speed of about 1000 rpm, at a temperature of between 10° C. and 40° C., advantageously between 15° C. and 30° C. and more particularly at ambient temperature (i.e. 23° C.±5° C.) for a time of between 15 s and 20 min and in particular between 30 s and 15 min.

Before step (b") or before step (c"), the method according to the invention may comprise an additional step consisting in eliminating any undissolved creatine fatty ester or salt thereof from the mixture obtained after step (a") or after step (b"). The conditions of this additional step are identical to the ones defined for the other alternatives of the method of the invention.

In addition, step (c") is conducted in conditions identical to the ones defined for the steps (d) and (d') of the other alternatives of the method of the invention.

The present invention also relates to a composition in the form of a micro-emulsion as previously defined for use in medicine.

Indeed, thanks to the in vivo investigations performed by the inventors, it is clear that the composition according to the invention can convey creatine fatty ester or salt thereof in the brain, in particular through peripheral or nasal administration, in order to restore creatine pool, since creatine fatty ester or salt thereof are degradable by plasma esterases in all biological fluids. The inventors have tested the efficacy of this composition in improving the brain performance of creatine transporter knock-out (CrT ko) mice and in particular their cognitive functions. It should be noted that the composition in the form of a micro-emulsion protects the creatine fatty ester or salt thereof it contains from degradation while administration to a subject.

Also disclosed is the use of such a composition in the form of a micro-emulsion able to by-pass the BBB in vivo without the involvement of Solute Large Carrier Transporter (SLC6A8) notably thanks to a nasal administration. So that creatine normally excluded by the BBB in patients with creatine transporter deficiency may be produced after cleavage of creatine fatty esters within the brain endothelial cells and released in the brain parenchyma.

Thus, the composition according to the present invention can be used in medicine and notably in therapeutic medicine, in medical diagnosis and in medical imaging such as by Positron Emission Tomography (PET). Indeed, the fact that the creatine part and/or the fatty ester part of the creatine fatty ester or of the salt thereof can present radioisotope(s) as previously disclosed can be useful in diagnosis and in imaging. For example, the glucosyl radical present in the compound according to the present invention can be substituted by at least one radioisotope such as $^{18}F$ for use in medical imaging and more particularly in PET.

The composition according to the present invention can be used for the treatment or the prevention of at least one disease, disorder or condition selected in the group consisting of a neuromuscular disorder, hypoxia, an ischemic brain disease such as stroke, an heart disease, a muscular dystrophy, a skin disorder and inflammation. In particular, the composition according to the present invention can be used for the treatment or the prevention of at least one disease, disorder or condition selected in the group consisting of a neuromuscular disorder, hypoxia and an ischemic brain disease such as stroke.

The composition according to the present invention can be used for the treatment of the brain creatine transporter deficiency disease.

In other words, the present invention concerns a method for treating or preventing at least one disease, disorder or condition selected in the group consisting of a neuromuscular disorder, hypoxia, an ischemic brain disease such as stroke, an heart disease, a muscular dystrophy, a skin disorder and inflammation, consisting in administering to a subject in need, a therapeutic amount of a composition according to the invention. More particularly, the present invention concerns a method for treating or preventing at least one disease, disorder or condition selected in the group consisting of a neuromuscular disorder, hypoxia and an ischemic brain disease such as stroke, consisting in administering to a subject in need, a therapeutic amount of a composition according to the invention.

The present invention also concerns a method for treating the brain creatine transporter deficiency disease, consisting in administering to a subject in need, a therapeutical amount of a composition according to the invention.

Additional information on such treatment methods can be found in [9] and in the bibliography cited therein, in particular, the documents referenced [1-4] in [9].

The composition according to the invention can be administered orally, nasally, parenterally (intravenous, intramuscular, or subcutaneous), topically, transdermally, intravaginally, intravesically, intracistemally, or rectally. Nasal administration is advantageous for any disease, disorder or condition affecting brain performance. Typically, a composition according to the invention will present a slightly acid pH value, in particular, a pH comprised between 4 and 6.9 and in particular between 4.5 and 6.5.

Other characteristics and advantages of the present invention will additionally be apparent to the one skilled in the art on reading the examples below, which are given as an illustration and not a limitation, with reference to the attached figures.

SHORT DESCRIPTION OF THE DRAWINGS

FIG. 1 presents the mean particle size and polydispersity index (PDI) of ME-1 and ME-2 after storage conditions.

FIG. 2 presents TEM photographs for ME-1 (FIGS. 2A and 2B) and ME-2 (FIGS. 2C and 2D) at different magnifications.

Figure 3:
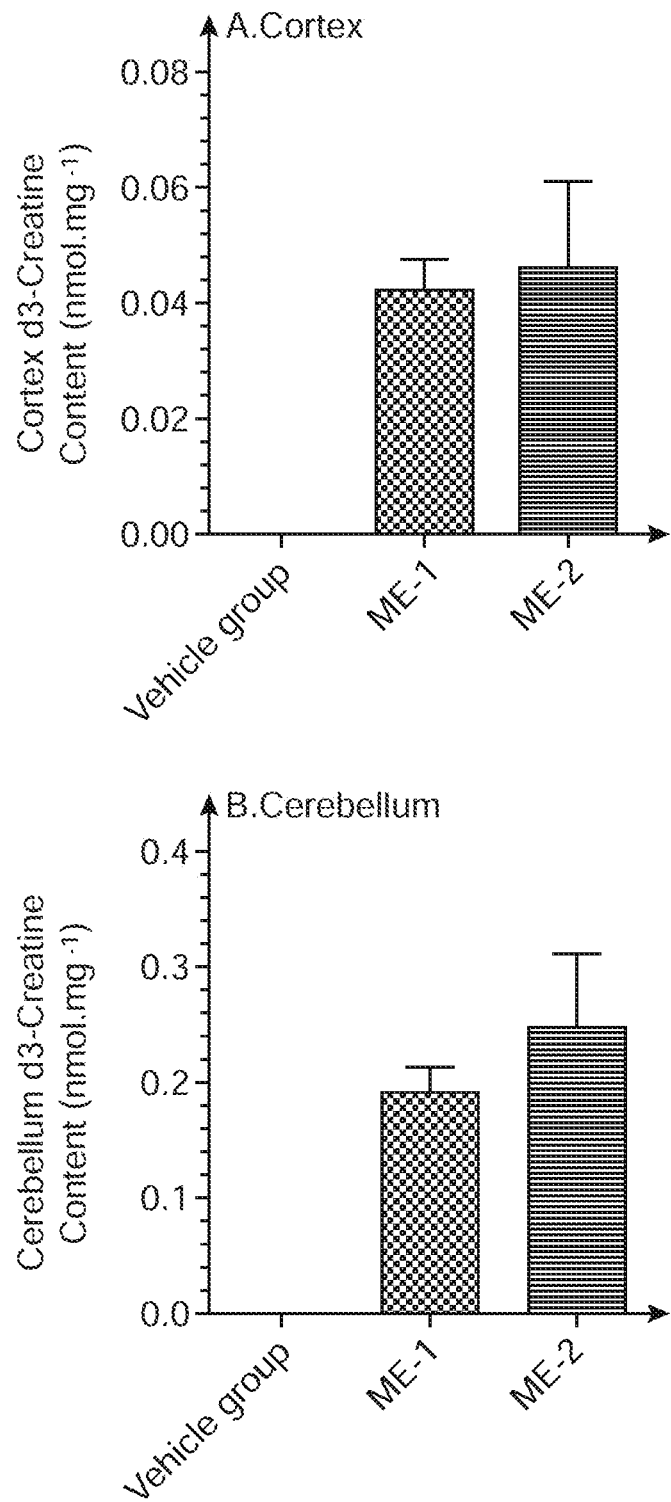

FIG. 3 presents creatine concentration in cortex and cerebellum tissue from mice following administration of DCE formulations by nasal route.

DETAILED DISCUSSION OF PARTICULAR EMBODIMENTS

I. Synthesis of Hydrochloride Salt of Creatine Dodecyl Ester ($DCE_{HCl}$).

DCE was prepared according to the method described in [9] and implemented in [10,11]. The chlorhydrate was obtained by dissolution in excess HCl 0.01 N and evaporation to dryness to give $DCE_{HCl}$.

II. Microemulsion of Hydrochloride Salt of Creatine Dodecyl Ester.

II.1. Solubility Studies.

Five mg of $DCE_{HCl}$ were introduced in different tubes containing 1 g of each tested oil or excipient. Then, the samples were vortexed and introduced in a Thermomixer C (Eppendorf, Montesson, France) at 37° C. and shaken at 1000 rpm for 48 h. The maximum solubility of DCE in oil or excipient was finally determined by LC-MS/MS following an adapted method previously described. Table 1 presents the results concerning the solubility of $DCE_{HCl}$ in the different excipients tested.

TABLE 1

Solubility of dodecyl creatine ester ($DCE_{HCl}$) in different excipients: oils, surfactants and co-surfactants for pharmaceutical applications $DCE_{HCl}$ Solubility (n = 3)

| Theoretical concentration: 5 mg/g | |
| --- | --- |
| Oils | DCE [mg/g] |
| Maisine ® CC | 2.78 ± 0.01 |
| Capmul MCM | 0.90 ± 0.01 |
| EP/NF/DHA | |
| Maisine/DHA (50/50) | 1.6 ± 0.1 |
| Surfactants | DCE [mg/g] |
| Capryol 90 | 3.3 ± 0.6 |
| Labrasol ALF | 3.3 ± 0.6 |
| Co-surfactant | DCE [mg/g] |
| Transcutol HP | 3.5 ± 0.3 |
| Vehicle: Maisine/DHA (50/50) | |
| Theoretical concentration (mg/g) | DCE [mg/g] |
| 10 | 0.3 ± 0.01 |
| 20 | 3.4 ± 0.2 |
| 40 | 3.9 ± 0.1 |

Among the lipids, Maisine® CC presents the highest solubility; thus, this lipid matrix was chosen for further studies. In order to evaluate the maximal solubility (saturation point), the same test was performed replacing the initial amount of $DCE_{HCl}$ by 10, 20 and 40 mg/g using Maisine CC/DHA as vehicle. The results showed that the initial concentration of 40 mg/g gave rise to the highest solubility of $DCE_{HCl}$ in this excipient.

In addition, Labrasol ALF and Transcutol HP were chosen for the micro-emulsions formulations based on the high solubility of $DCE_{HCl}$ in these excipients and the safety properties.

II.2. Preparation of $DCE_{HCl}$ Micro-Emulsion.

The lipid formulation was prepared by a simple one step method. Briefly, 40 mg of $DCE_{HCl}$ were added with 1 g of an oily glyceride-based excipient to reach a final theoretical concentration of 40 mg/g. The mixture was vortexed for 5 min and shaken in a thermomixer (1000 rpm at 37° C.) for 48 h. Then, a centrifugation process (20 000 g-15 min at 20° C.) was applied and the supernatant was filtered through a 0.22 µm filter, placed in another tube and storage at room temperature prior to use.

Then this initial mix was added with a fixed amount of DHA and vortexed for 1 min. The emulsification method used was the titration technique. The oil phase ($DCE_{HCl}$, Maisine CC and DHA) was added with surfactant (Transcutol HP) or surfactant mix (1:1, Labrasol ALF:Transcutol-HP) and stirred continuously on magnetic stirrer (Stuart CB162, Bibbly Scientific, Nemours, France) at stirred 5 for 5 min at room temperature. Fixed amount of distilled water was added dropwise to the above mixture and stirred continuously in the same technical conditions described above until transparent and homogeneous micro-emulsion (ME) was produced. Table 2 presents the composition of the two final chosen formulations based on water and surfactants contents (ME-1 and ME-2). The amounts given in Table 2 are amounts in weight based on the total weight of the micro-emulsion containing neither creatine fatty ester, nor creatine fatty ester salt.

TABLE 2

Composition of micro-emulsion for DCE loading

| Components | ME-1 (% w/w) | ME-2 (% w/w) |
| --- | --- | --- |
| Maisine CC | 10.52 | 5.88 |
| DHA | 5.26 | 11.76 |
| Labrasol ALF | 28.95 | — |
| Transcutol-HP | 28.95 | 64.71 |
| Milli Q water | 26.32 | 17.65 |

II.3. Physical-Chemical Characterization of $DCE_{HCl}$ Micro-Emulsions.

Particle size and polydispersity index (PDI) of $DCE_{HCl}$-ME were determined by dynamic light scattering (DLS) using a Vasco Flex nanoparticle size analyzer (Cordouan Technology (Pessac, France). Samples were diluted to an appropriate concentration in deionized water and each analysis was carried out in triplicate at 25° C. with a detection angle of 173°.

FIG. 1 presents the mean diameter of particle from ME-1 and ME-2 measured at 0, 7, 15 and 30 days and storage at 4-8° C. It should be noticed that no precipitation was observed and ME presented an average particle size around 150-170 nm for ME-1 and 90-100 nm for ME-2 and a very narrow size dispersion (PDI≤0.2) for both formulations which account for its homogeneity and stability at long terms.

The pH of the formulations was also determined by using an Inolab pH730 pH-meter with a probe sentix 41 (Apeldoorn, Holland). The formulations presented a slightly acid pH value (5.07 and 4.73 for ME-1 and ME-2 respectively). Taking into account that the nasal mucosal pH is approximately 5.5-6.5, no irritation or local inflammation should occur after an in vivo administration of our formulations.

II.4. Stability Studies.

The stability of $DCE_{HCl}$-ME was evaluated over 1 month upon storage conditions (4-8° C.) to ensure that neither leakage, nor degradation of the drug occurred during storage. The $DCE_{HCl}$ was quantified by liquid chromatography coupled to mass spectroscopy (LC/MS-MS) following a previous developed method [10]. Measures were determined in triplicate after centrifugation (20 000 g-15 min at 20° C.). Table 3 presents the loading for both formulations at 0, 7, 15 and 30 days.

TABLE 3

Stability of $DCE_{HCl}$ loading in ME-1 and ME-2 over 30 days at storage conditions

| Formulation | $DCE_{HCl}$ concentration (mg/g) | | | |
| --- | --- | --- | --- | --- |
| | 0 | 7 days | 15 days | 30 days |
| ME 1 | 2.87 ± 0.12 | 2.15 ± 0.09 | 2.16 ± 0.05 | 1.41 ± 0.05 |
| ME 2 | 3.93 ± 0.05 | 3.52 ± 0.18 | 2.92 ± 0.02 | 2.39 ± 0.12 |

II.5. Microscopy Analyses.

The morphological structures of ME were investigated using a LVEM5 transmission electron microscope (Cordouan technologies, Pessac, France). The formulations were diluted (1:50) in distilled water and an ELMO glow discharge system for EM grids was applied following the manufacturer protocol.

The morphological appearance of ME-1 and ME-2 are shown in FIGS. 2A and 2B and FIGS. 2C and 2D respectively. It could be observed that both types of ME structures presented a spherical morphology with a narrow size distribution suggesting that the micro-emulsions were dispersed homogeneously in aqueous medium. The particles appeared dark with bright surroundings, and no aggregation was seen.

III. In Vivo Test of Nasal Administration.

The nasal route was adopted to exploit first its avoidance of the hepatic first-pass metabolism to increase the absolute bioavailability, and second the direct nose-to-brain pathway to enhance the brain drug delivery. The aim of this test was to evaluate the non-toxicity of the formulations according to the present invention and the ability of $DCE_{HCl}$ to be translocated to the brain and turn into creatine.

For this purpose, nine wild type C57BL/6 female mice (weight: 20-30 g) were used in the study. The mice were divided into 2 groups. Group 1 received ME-1 and Group 2 received ME-2. One mouse from each group received only the vehicle as control.

Regarding the high endogen creatine content in wild type, the formulations were prepared with deutered DCE (DCE-d3) in order to quantify then the deutered creatine (Creatine-d3) which would be only detected in treated animals and independent of endogen creatine concentration.

The dose was given as nasal drops using a micropipette, divided equally into two nostrils (24 μl final volume) for 5 consecutive days. Every day the animals were examined for any abnormal behavior, mortality and morbidity. At the end of the treatment, mice were sacrificed by cervical dislocation. Samples (cortex and cerebellum) were weighed and collected in tubes and storage at −80° C. prior to analysis. For LC/MS/MS quantifications the previously developed technique for Creatine brain analysis [10] was adapted.

No mortality was observed in any of the groups during the 5-day treatment period Macroscopic examination of the brain sections exposed to the formulations did not show any change in the morphology or tissue microstructure as compared to normal control group mouse. No visible sign of inflammation or necrosis revealed the safety of the developed formulations.

FIG. 3 shows the mean Creatine-d3 concentration per mg of protein in cortex and cerebellum tissues. These results clearly showed that when administered through nasal route, all the developed formulations were found to be effective in enhancing brain targeting and thus the existence of a direct nose-to-brain delivery route for $DCE_{HCl}$ formulations.

REFERENCES

[1] International application WO 02/22135 in the name of Board of Regents of the University of Nebraska, published on Mar. 21, 2002.
[2] Patent application US 2002/0049253 in the name of Kaddurah-Daouk, published on Apr. 25, 2002.
[3] Patent application US 2003/0212130 in the name of Miller et al, published on Nov. 13, 2003.
[4] International application WO 2015/120299 in the name of University of Utah Research Foundation, published on Aug. 13, 2015.
[5] Stöckler et al, 2007, "Cerebral creatine deficiency syndromes. Clinical aspects, treatment and pathophysiology", Subcell. Biochem., vol. 46, pages 149-166.
[6] van de Kamp et al, 2014, "X-linked creatine transporter deficiency: clinical aspects and pathophysiology", J Inherit Metab Dis., vol. 37, pages 715-733.
[7] Kurosawa et al, 2012, "Cyclocreatine treatment improves cognition in mice with creatine transporter deficiency", J. Clin. Invest., vol. 122, pages 2837-2846.
[8] Patent application US 2015/0238453 in the name of 4141 HOLDINGS, LLC, published on Aug. 27, 2015.
[9] Patent application EP 2 692 719 in the name of Commissariat à l'Energie Atomique et aux Energies Alternatives, published on Feb. 5, 2014.
[10] Trotier-Faurion et al, 2013, "Synthesis and biological evaluation of new creatine fatty esters revealed dodecyl creatine ester as a promising drug candidates for the treatment of the creatine transporter deficiency", J. Med. Chem., vol. 56, pages 5173-5181.
[11] Trotier-Faurion et al, 2013, "Dodecyl creatine ester and lipid nanocapsule: a double strategy for the treatment of creatine transporter deficiency", Nanomedicine, vol. 10, pages 185-191.
[12] Patent application EP 0 589 843 in the name of Sandoz AG, published on Mar. 30, 1994.

What is claimed is:

1. A nasal composition in the form of a micro-emulsion for nasal administration, wherein said composition comprises (i) an oil phase comprising at least one omega 3 fatty acid or salt thereof and at least one glyceride, (ii) an aqueous phase and (iii) at least one non ionic surfactant(s), wherein said composition has a pH of from 4.5-6.5 and further comprises at least one creatine fatty ester or salt thereof.

2. The composition according to claim 1, wherein said at least one creatine fatty ester is represented by the formula (I):

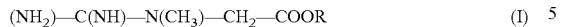

in which R represents an alkyl radical with 4 to 30 carbon atoms, an alkenyl radical with 4 to 30 carbon atoms, an aryl radical with 6 to 30 carbon atoms or a glucosyl radical optionally substituted.

3. The composition according to claim 1, wherein said at least one creatine fatty ester or salt thereof is dodecyl creatine ester or hydrochloride salt of dodecyl creatine ester.

4. The composition according to claim 1, wherein said at least one creatine fatty ester or salt thereof is present in an amount of 0.01% to 6% by weight based on the total weight of the composition.

5. The composition according to claim 1, wherein said at least one omega-3 fatty ester or salt thereof is docosahexaenoic acid (DHA).

6. The composition according to claim 1, wherein said at least one omega-3 fatty ester or a salt thereof is present in an amount of 4% to 13% by weight based on the total weight of the composition.

7. The composition according to claim 1, wherein said at least one glyceride is a mixture of mono-, di- and triglycerides of linoleic ($C_{18:2}$) and oleic ($C_{18:1}$) acids.

8. The composition according to claim 1, wherein said at least one glyceride is present in an amount of 4% to 13% by based on the total weight of the composition.

9. The composition according to claim 1, wherein said at least one non-ionic surfactant is selected from the group consisting of polyoxyethylene sorbitan monoesters; polyethoxylated oils; polyethylene oxides; propylene glycol esters of fatty acids; polyoxylglycerides and polyethoxylated alcohols.

10. The composition according to claim 1, wherein said at least one non-ionic surfactant is a mixture of one polyoxylglyceride and one polyethoxylated alcohol.

11. The composition according to claim 1, wherein said at least one non-ionic surfactant is present in an amount of 50% to 68% by weight based on the total weight of the composition.

12. The composition according to claim 1, wherein said aqueous phase is present in an amount of 15% to 30% by weight based on the total weight of the composition.

13. A method for preparing the composition in the form of a micro-emulsion as defined in claim 1, wherein said method comprises the following steps:
    a) preparing the oil phase by mixing at least one omega 3 fatty acid or salt thereof and at least one glyceride,
    b) adding, to the oil phase prepared at step (a), the at least one creatine fatty ester or salt thereof and mixing in order to obtain an oil phase in which the at least one creatine fatty ester or salt thereof is dissolved,
    c) adding, to the oil phase prepared at step (b), the at least one non-ionic surfactant and mixing to form a mixture,
    d) adding, to the mixture prepared at step (c), the aqueous phase and mixing, whereby the composition in the form of a micro-emulsion is obtained.

14. A method for preparing the composition in the form of the micro-emulsion as defined in claim 1, wherein said method comprises the following steps:
    a') mixing the at least one creatine fatty ester or salt thereof and the at least one glyceride to form a first mixture,
    b') adding, to the first mixture prepared at step (a'), the at least one omega 3 fatty acid or salt thereof and mixing in order to obtain the oil phase in which the at least one creatine fatty ester or salt thereof is dissolved,
    c') adding, to the oil phase prepared at step (b'), the at least one non-ionic surfactant and mixing to form a second mixture,
    d') adding, to the second mixture prepared at step (c'), an aqueous phase and mixing, whereby the composition in the form of a micro-emulsion is obtained.

15. A medicinal composition comprising the micro-emulsion as defined in claim 1.

16. A method of treating at least one disease, disorder or condition selected from the group consisting of a neuromuscular disorder, hypoxia, an ischemic brain disease, a heart disease, a muscular dystrophy, a skin disorder and inflammation, comprising administering the medicinal composition according to claim 15.

17. A method of treating a brain creatine transporter deficiency disease comprising administering the medicinal composition according to claim 15.

18. The composition according to claim 6, wherein said at least one omega-3 fatty ester or a salt thereof is present in an amount of 5% to 12% by weight based on the total weight of the composition.

19. The composition according to claim 11, wherein said at least one non-ionic surfactant is present in an amount of 58% to 65% by weight based on the total weight of the composition.

20. The composition according to claim 12, wherein said aqueous phase is present in an amount of 18% to 27% by weight based on the total weight of the composition.

21. The composition according to claim 1, having an average particle size of less than 200 nm.

22. The composition according to claim 21, wherein the polydispersity index (PDI) of the composition, as determined by dynamic light scattering in water with a detection angle of 173°, is ≤0.2.

23. A nasal composition in the form of a micro-emulsion comprising (i) an oil phase comprising at least one omega 3 fatty acid or salt thereof and at least one glyceride, (ii) an aqueous phase and (iii) one or more non-ionic surfactant(s) selected from the group consisting of polyoxyethylene sorbitan monoesters; polyethoxylated oils; polyethylene oxides; propylene glycol esters of fatty acids; polyoxylglycerides, polyethoxylated alcohols and mixtures thereof, said composition containing at least one creatine fatty ester or salt thereof and wherein said composition has a pH of from 4.5-6.5.

24. A nasal composition in the form of a micro-emulsion for nasal administration, wherein said composition comprises (i) an oil phase comprising at least one omega 3 fatty acid or salt thereof in an amount of from 4% to 13% by weight based on the total weight of the composition, and at least one glyceride in an amount of from 4% to 13% by weight based on the total weight of the composition, (ii) an aqueous phase in an amount of from 15% to 30% by weight based on the total weight of the composition and (iii) one or more non ionic surfactant(s) in an amount of from 50% to 68% by weight based on the total weight of the composition, said composition further comprising at least one creatine fatty ester or salt thereof in an amount of 0.01% to 6% by weight based on the total weight of the composition.

25. The composition according to claim 24, wherein said composition has a pH of from 4.5-6.5.

* * * * *